United States Patent [19]
Dodd et al.

[11] Patent Number: 5,484,793
[45] Date of Patent: Jan. 16, 1996

[54] COMPOUNDS DERIVED FROM 6-AZAINDOLES AS LIGANDS OF THE BENZODIAZEPINE RECEPTOR AND MEDICAMENTS CONTAINING THEM

[75] Inventors: Robert H. Dodd; Pierre Potier, both of Paris; Xavier Doisy, Versailles; Jean Rossier; Lia P. De Carvalho, both of Paris, all of France

[73] Assignee: Centre National de la Recherche Scientifique (CNRS), Paris, France

[21] Appl. No.: 142,489

[22] PCT Filed: May 29, 1992

[86] PCT No.: PCT/FR92/00480

§ 371 Date: Nov. 29, 1993

§ 102(e) Date: Nov. 29, 1993

[87] PCT Pub. No.: WO/9221680

PCT Pub. Date: Dec. 10, 1992

[30] Foreign Application Priority Data

May 29, 1991 [FR] France ..................... 91 06453

[51] Int. Cl.⁶ ............. C07D 471/04; C07D 471/06; A61K 31/44
[52] U.S. Cl. ............................... 514/300; 546/113
[58] Field of Search .............................. 546/113; 514/300

[56] References Cited

FOREIGN PATENT DOCUMENTS 0217737  6/1988  European Pat. Off. .

OTHER PUBLICATIONS

Tetrahedron, vol. 46, No. 9, 1990, pp. 3245–3266.
Dellouve–Courillon, "Synthesis of B–Carboline–Benzodiazepine . . . ", Tetrahedron, vol. 46, No. 9, pp. 3245–3266, 1990.
Smart, "Synthesis of Functional . . . ", Neuroscience Letters, vol. 40, pp. 55–59, 1983.
Sigel, "Allosteric Modulation by Benzodiazepine Receptor . . . ", Journal of Neuroscience, vol. 8(1), pp. 289–295, 1988.
Shutske, "9–Amino–1,2,3,4–tetrahydroacridin–1–osl: Synthesis . . . ", J. Med. Chem., vol. 32, pp. 1805–1813, 1989.
Kawakubo, "Potent Anticonflict Activity . . . ", J. Med. Chem., vol. 33, pp. 3110–3116, 1990.
Sasaki, "Synthesis and Anticonvulsant Activity . . . ", J. Med. Chem., vol. 34, pp. 628–633, 1991.
Venault, "Benzodiazepine Impairs and . . . ", reprinted from Nature, vol. 321, No. 6073, pp. 864–866, 1986.
File, "Low and High Doses . . . ", Behavioural Brain Research, vol. 30, pp. 31–36, 1988.
Jensen, "Bidirectional Effects of . . . ", Brain Research Bulletin, vol. 19, pp. 359–364, 1987.
Duka, "Human Studies on the Benzodiazepine Receptor . . . ", Psychopharmacology, vol. 93, pp. 421–427, 1987.
Sarter, "Treatment Strategies for Senile Dementia . . . ", TINS, vol. 11, No. 1, pp. 13–16, 1988.
Hendrickson, James B., *Organic Chemistry, third edition*, pp. 403–404, 504–506 and 515, 1970.
Solomons, T. W. Graham, *Organic Chemistry, foruth edition*, pp. 837–838 and 862, 1988.

Primary Examiner—C. Warren Ivy
Assistant Examiner—D. Margaret M. Mach
Attorney, Agent, or Firm—Jacobson, Price, Holman & Stern

[57] ABSTRACT

New 6-azaindole derivatives as ligands of the benzodiazepine receptor, pharmaceutical compositions containing these compounds, processes for producing these compounds and also compounds which are useful in particular as intermediates in the processes of preparation.

14 Claims, No Drawings

COMPOUNDS DERIVED FROM 6-AZAINDOLES AS LIGANDS OF THE BENZODIAZEPINE RECEPTOR AND MEDICAMENTS CONTAINING THEM

This application is a 371 of PCT/FR92/00480, filed 29 May 1992.

The invention relates to new 6-azaindole derivatives as ligands of the benzodiazepinee receptor, to the pharmaceutical compositions containing these compounds, to the processes for producing said compounds and also to the compounds which are useful in particular as intermediates in the processes of preparation.

1,4-Benzodiazepines (for example Valium) constitute a class of widely-prescribed medicaments due to their anxiolytic, anticonvulsant, sedative/hypnotic and muscle relaxant activities. The mechanism of action of the benzodiazepines remained unrecognized for a long time until the discovery of specific binding sites (or "receptors") for these molecules on the neuronal membranes of the central nervous system. The physiological importance of these receptors was demonstrated by the existence of good correlation between, on the one hand, the value of the affinity of the various benzodiazepines for the receptor (measured by displacement of a radioactive benzodiazepine) and, on the other hand, their therapeutic effectiveness.

Likewise, it was found that certain β-carbolines behaved as agonists of the benzodiazepine receptor.

Thus, Abecarnil, developed by Schering as an anxiolytic,

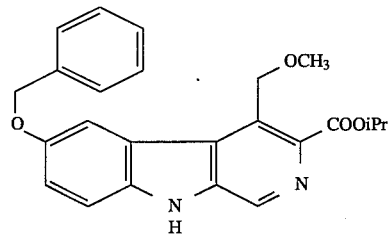

Abecarnil

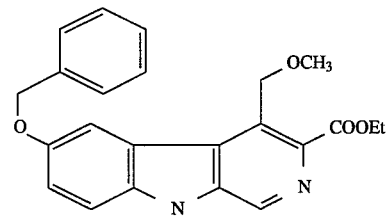

ZK 93423

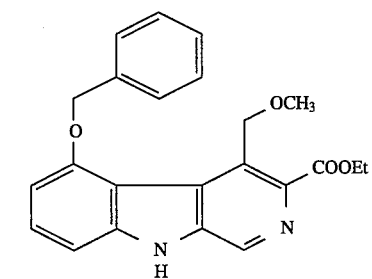

ZK 91926 is in the course of clinical trials. Other related β-carboniles such as ZK 93423 and ZK 91296 also possess properties analogous to those of diazepam in vivo (anxiolytic, anticonvulsant, and the like).

While searching for an endogenous ligand of the benzodiazepine receptor, Braestrup et al. (Proc. Natl. Acad. Sci., USA, 77, 2288–2292, 1980) discovered a molecule, the ethyl ester of β-carboline-3-carboxylic acid (β-CCE), extracted from human urine, which binds with very good affinity to the central receptors of benzodiazepines ($IC_{50}=4$ nM, in vitro, rat brain). On the other hand, β-CCE has pharmacological effects in vivo which are opposite to those of the benzodiazepines. Thus, β-CCE is a proconvulsant in mice, facilitating the convulsions caused by other agents such as pentylenetetrazole.

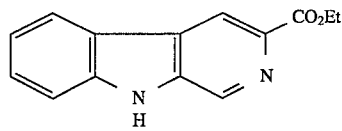

The term "inverse agonist" is now used to denote these ligands of the benzodiazepine receptor which have activities completely or partially opposed to those of the benzodiazepines.

The therapeutic advantage of the β-carbolines lies at several levels. Thus, the team which is the author of the present invention was the first to demonstrate that such molecules (for example β-CCM below),

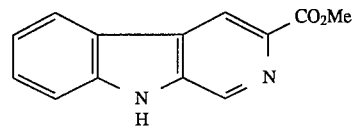

inverse agonists of the benzodiazepine receptor, have a positive effect on learning and memory (Venault et al., Nature, 321, 864–866, 1986). Although β-CCM could not be tested in man for its memory-enhancing effects due to its highly convulsant activity, other analogues such as ZK 93426 or Flumazenil, which are antagonists of the benzodiazepine receptor, were tested in man where their memory-enhancing properties were revealed (Duka et al., Psychopharmacology, 93, 42–427, 1987 and Lal et al., Pharmacol, Biochem. Behav., 35, 747–750, 1990).

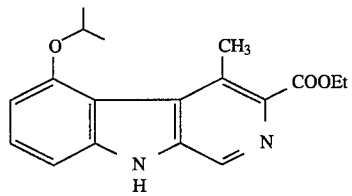

ZK 93426

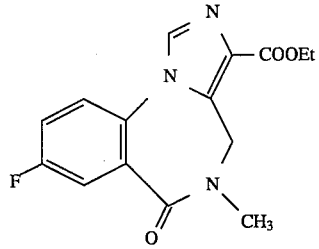

Flumazenil

Thus, it would seem that antagonists or partial inverse agonists of the benzodiazepine receptor are useful in the treatment of certain cognitive problems such as Alzheimer's disease.

Moreover, 6-azaindole derivatives are known, some of which have been tested for their suitability on the central nervous system.

Thus, the authors of the present invention have described the synthesis of 2,5-dicarbethoxy-6-azaindole by the Frydman method (Dodd et al., Heterocycles, 28, 1101–1113, 1989). This molecule only has a very weak affinity for the benzodiazepine receptor in vitro ($IC_{50}=84,000$ nM).

Other compounds have been described by some of the authors of the invention in collaboration with other researchers (Dodd et al., J. Med. Chem., 32, 1272–1276, 1989 and Dellouve-Courillon et al., Tetrahedron, 46, 3245–3266, 1990).

However, no indication regarding their properties with respect to benzodiazepine receptors was reported.

For example, the compound of formula:

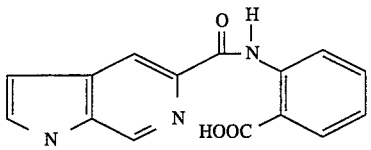

was described in the abovementioned publication by Dellouve-Courillon.

Likewise, the 6-azaindoles (mono-, di- and trisubstituted) mentioned below have been described in the literature (Frydman et al., J. Am. Chem. Soc., 87, 3530–3531, 1965; Frydman et al., J. Org. Chem., 33, 3762–3766, 1968; Fischer et al., J. Med. Chem., 15., 1168–1171, 1972; Prokopov et al., Chem. Het. Compounds, 4, 406–410, 1978; Clark et al., J. Chem. Soc., (C), 498–501, 1970; Fischer et al., J. Het. Chem., 6, 775–776, 1969; Yakhontov et al., Russian Chem. Rev., 49, 428–444, 1980).

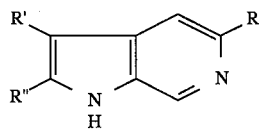

R=H, OCH$_3$, OCH$_2$C$_6$H$_5$

R'=H, CH$_2$CH$_2$CO$_2$H, CH$_2$N(CH$_3$)$_2$, CHO, CH=NOH CN, CH$_3$, CH$_2$NH$_2$, NO$_2$, Br

R"=H, CO$_2$H, CO$_2$C$_2$H$_5$, CONH$_2$, CN, C$_6$H$_5$, CHO, CH$_2$OH

None of these molecules is known for interacting with the benzodiazapin receptor.

Finally, Patent DE-A-3,525,928 describes the synthesis of 5,6,7,8-tetrahydro-β-carboline derivatives.

Consequently, one of the aims of the present invention is to propose new compounds having an affinity with the benzodiazapin receptor while having an at least partial inverse agonist effect.

Another aim of the present invention is to propose new therapeutic compositions which are useful in particular in the treatment of nervous disorders.

Another aim of the present invention is to propose new therapeutic compositions having a positive effect on learning and memory and which can be used for the treatment of cognitive problems such as, for example, in Alzheimer's disease.

The invention relates, in the first place, to the 6-azaindole of formula:

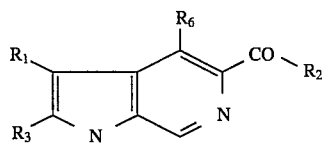

in which:

R$_1$ represents the hydrogen atom or a group R$_5$—O—CH$_2$— in which R$_5$ corresponds to an alkyl radical optionally substituted by one or a number of alkoxy, alkylthio, alkylcarbonyl, amino, nitro or cyano groups or a to a group of formula Ar—Z, in which:

Z is a saturated or unsaturated divalent radical having from 1 to 5 atoms preferably chosen from —CH$_2$—, —CH$_2$CH$_2$—, —CH=CH— or —CH=CH—CH$_2$—, Ar is an optionally substituted phenyl or heteroaryl radical containing 5 to 6 atoms in the ring including 1 to 3 heteroatoms, R$_2$ is an alkoxy, cycloalkoxy, aryloxy, aralkoxy, N-alkyl-substituted amino, N-cycloalkyl-substituted amino or N-phenyl-substituted amino radical, it being possible for the aromatic parts to be optionally substituted, R$_3$, R$_4$ independently represent the hydrogen atom or an alkyl radical, with the exception of the compound where R$_1$, R$_3$ and R$_4$ are the hydrogen atom and R$_2$ is the N-(2-carboxyphenyl)amino radical, and the pharmacologically acceptable salts of these compounds.

In the present description, the alkyl or alkoxy radicals preferably have from 1 to 6 carbon atoms and can be linear or branched (preferably linear). The aryl or aryloxy radicals preferably have 6 to 10 carbon atoms and the aralkyl or aralkoxy radicals from 7 to 11 carbon atoms.

Mention may be made, among the heteroaryl radicals, of the 1- or 2- or 3-pyridyl, 1- or 2- or 3-pyrrolyl, 2- or 3-thienyl, 2- or 3-furyl, or 1- or 2- or 3- or 4-imidazolyl radicals or the various pyrimydinyl radicals.

Mention may be made, among the substituents of the phenyl or heteroaryl compounds, of weakly hindered donor radicals such as halogen atoms or nitro, cyano, optionally halogenated alkoxy, optionally halogenated C$_1$-C$_3$ alkyl, linear in the case of C$_3$, CF$_3$ in particular, or SO$_3$H radicals.

Moreover, certain compounds have one or a number of asymmetric centres. They can therefore exist in one or a number of optically active forms. In this case, the invention comprises said optically active forms of these compounds.

Mention may be made, among these salts, of: chlorides, hydrochlorides, tartrates or fumarates.

According to a preferred variant, the R$_1$ group corresponds to the group of formula

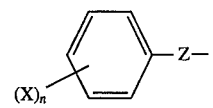  II in which:

X is a weakly hindered electron-donating radical, n is a positive integer or zero, less than 6, it being possible for the X groups to be identical or different when n is greater than 1.

Mention may be made, among the electron-donating X radicals, preferably of halogen atoms or nitro, cyano, optionally halogenated alkoxy, optionally halogenated C$_1$-C$_3$ alkyl, linear in the case of C$_3$, in particular CF$_3$, or SO$_3$H radicals and preferably n=0, 1, 2 or 3.

According to a preferred variant, the R$_1$ group corresponds to the group of formula III:

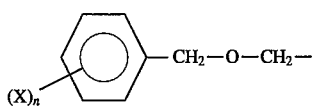  III or R$_1$ is a methyl group substituted by an alkoxy radical and COR$_2$ is preferably an ester functional group.

According to another preferred variant, R$_1$ is a hydrogen atom and COR$_2$ is preferably an amide functional group, R$_2$ advantageously being an N-aryl amide, in particular N-phenylamide, optionally substituted by one or a number of radicals chosen from carboxyl, sulfonate or acid phosphonate radicals.

It has in fact been found, in an entirely unexpected way, that certain amides according to the invention showed affinities with respect to rat cortex which were greater than those of the esters.

Furthermore, in the β-CCM series, for the first time molecules have been provided containing an amide group which have good properties with respect to the desired goal. These molecules additionally have a number of advantages:

a better hydrolytic stability;

a new point of interaction with the benzodiazepine receptor.

The invention also relates to the processes for the preparation of the compounds according to the invention.

In the description which follows, except when otherwise indicated, the $R_1$ to $R_5$ substituents have the same meaning as above.

a) process for the preparation of the compounds of formula I in which $R_2$, $R_3$ and $R_4$ have one of the meanings indicated above and $R_1$ corresponds to the $R_5$—$OCH_2$ group.

This process consists in reacting a compound of formula:

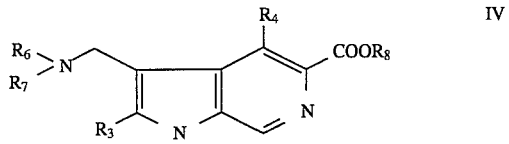

in which $R_6$ and $R_7$ are independently the hydrogen atom or a $C_1$-$C_4$ alkyl radical, $R_8$ is $(C_1$-$C_4)$alkyl, $(C_3$-$C_6)$cycloalkyl, $(C_6$-$C_{10})$aryl or $(C_7$-$C_{11})$aralkyl, the aromatic rings optionally being substituted as for $R_2$, in the presence of the sodium salt of a carboxylic acid $R_9COOH$ ($R_9$=$C_1$-$C_4$ alkyl), in particular acetic acid, in the corresponding anhydride at reflux in order to obtain the compound of formula:

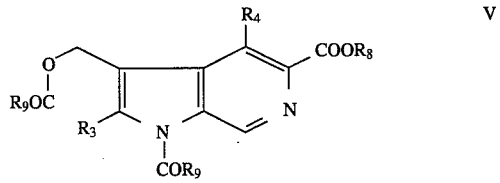

and in then reacting the latter compound with an alcohol $R_5OH$, in the presence of a weak acid (for example paratoluenesulfonic acid) and a polar aprotic solvent such as acetonitrile, which leads to the desired compound of formula I. The ester function group at the 5 position is converted to an amide functional group in a known way. It is also possible, in a first step, to convert the $COOR_8$ ester group to an amide group (compound Va) and then to react the $R_5OH$ group.

The compound of formula IV is prepared by reacting a compound of formula:

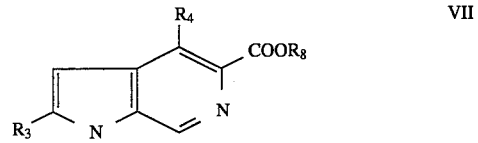

with a halide of a

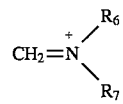

cation in a known way.

b) Process for the preparation of the compounds of formula I in which:

$R_2$, $R_3$ and $R_4$ have one of the meanings indicated above and $R_1$ corresponds to the hydrogen atom.

This process consists in converting the compound of formula:

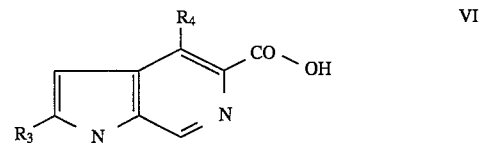

to an amide or ester functional group in a known way.

For example, production of the amide functional group is assured according to the instructions of the abovementioned publication by Dellouve-Courillon.

Thus, one of the subjects of the invention is also the compounds of formula:

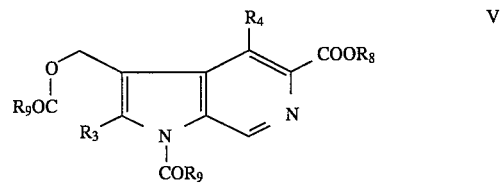

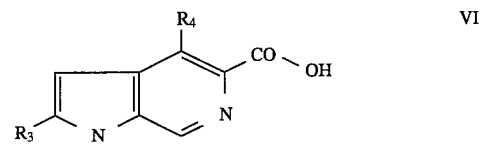

and Va which are useful in particular as intermediates in the preparation processes indicated above.

The compound of formula VII is prepared by esterification of the corresponding acid VI which is itself prepared by oxidation of the aldehyde VIII. The latter is obtained in a known way, for example according to the reaction scheme described in the abovementioned publication by Dellouve-Courillon et al.

The invention also relates to the medicaments consisting of one of the compounds according to the invention and the compound of formula I in which $R_1$, $R_3$ and $R_4$ are the hydrogen atom and $R_2$ the N-(2-carboxyphenyl)amino radical such as have just been described above and to the pharmaceutical compositions containing at least one of these medicaments and an acceptable vehicle. These medicaments and compositions are useful for the medical or veterinary treatment of certain disorders related to the functioning of the nervous system.

These medicaments and compositions are particularly intended to be used in combination with benzodiazapins in order to compensate for the harmful effects due to the use of the latter. These compounds themselves also promote learning and the retention of information in man.

These medicaments and compositions can thus be advantageously intended to participate in an effective therapy against degenerative diseases of the nervous system, in particular Alzheimer-type dementias.

The pharmaceutical compositions are in particular formulated to be ingested orally or to be injected. Nevertheless, other presentations can also be envisaged within the context of the present invention.

The dosage will depend partly on the illness to be treated and on its seriousness and also on the type of the individual (weight, age).

A dosage ranging from 0.1 mg/kg to 20 mg/kg could advantageously be envisaged.

The examples below illustrate the invention:

EXAMPLE 1

Preparation of Methyl 3-Benzyloxymethyl-6-Azaindole-5-Carboxylate

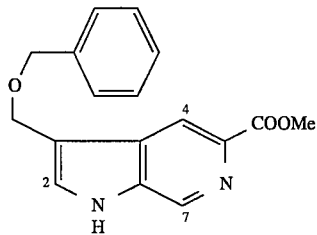

A—Preparation of Methyl 3-(N,N-Dimethylaminomethyl)- 6-Azaindole-5-Carboxylate

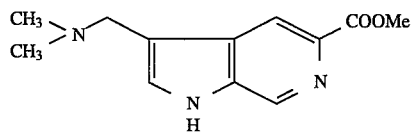

234.4 (2.50 mmol) of N,N-dimethylmethyleneiminium chloride are added to 296.0 mg (1.68 mmol) of ester ($R_1=R_3=R_4$ H, $R_2OCH_3$) in 30 ml of dry acetonitrile and the mixture is maintained at reflux overnight. The progress of the reaction is monitored by TLC (80/20 chloroform/methanol). The reaction mixture is then cooled and concentrated under vacuum. It is then basified with a saturated sodium bicarbonate solution and then extraction is carried out with dichloromethane. The organic phases are combined, washed with water and then a sodium chloride solution [lacuna] is dried over magnesium sulfate. The solvent is evaporated under reduced pressure, leaving a residue which is crystallized from a mixture of dichloromethane and acetonitrile to lead to 171.2 mg (43%) of azagramine.

M.p. (dichloromethane/acetonitrile)=217° C.

B—Preparation of Methyl N-Acetyl-3-Acetoxymethyl-6-Azaindole-5-Carboxylate

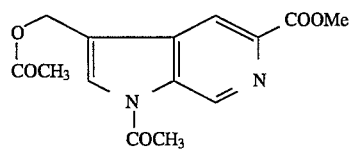

51.2 mg (0.22 mmol) of the above azagramine and 44.6 mg (0.54 mmol) of anhydrous sodium acetate are dissolved in 1 ml of distilled acetic anhydride and the mixture is maintained at reflux for 1 hour. The progress of the reaction is monitored by TLC (80/20 chloroform methanol) and, when it is complete, the reaction mixture is cooled. It is then neutralized with a saturated sodium bicarbonate solution and extracted with dichloromethane. The organic phases are combined, washed with water and dried over magnesium sulfate. The solvent is evaporated under reduced pressure, leaving a residue which is chromatographed on a preparative plate (97.5/2.5 dichloromethane/ethanol) to lead to the diacetylated derivative which is crystallized from a mixture of chloroform, ethyl acetate and nHexane (50.4 mg: 79%).

M.p. (chloroform/ethyl acetate/n-Hexane)= 170°–172° C.

C—Preparation of Methyl 3-Benzyloxymethyl-6-Azaindole- 6-Carboxylate

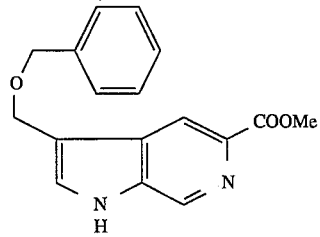

9.6 mg (0.03 mmol) of the above diacetate, 9.8 mg (0.05 mmol) of paratoluenesulfonic acid monohydrate and 4.1 μl (0.04 mmol) of benzyl alcohol in 3 ml of dry acetonitrile are maintained at reflux for 48 hours. The disappearance of the starting material is monitored by TLC (90/10 dichloromethane/ethanol). The solution is cooled, basified with a saturated sodium bicarbonate solution and extracted with dichloromethane. The organic phases are combined, washed with water and then with a saturated sodium chloride solution, dried over magnesium sulfate and then evaporated under vacuum. The residue is chromatographed on a preparative plate (90/10 dichloromethane/ethanol) and then crystallized from a mixture of chloroform and n-Hexane, leading to 5.4 mg (55%) of the 3-benzyloxymethyl derivative.

M.p. (chloroform/n-Hexane)=191° C.

By employing the same synthetic process, but with suitable starting materials, the following compounds were obtained:

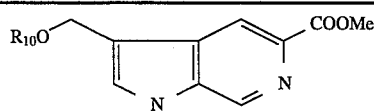

| Examples | $R_{10}$ | °M.p. [sic] |
| --- | --- | --- |
| 2 | $CH_3$ | 156 |
| 3 | $2F-PhCH_2$ | 193 |
| 4 | $3F-PhCH_2$ | 171 |
| 5 | $4F-PhCH_2$ | 201 |
| 6 | $2NO_2-PhCH_2$ | 266 |
| 7 | $3NO_2-PhCH_2$ | 260 |
| 8 | $4NO_2-PhCH_2$ | 238 |
| 9 | $3MeO-PhCH_2$ | 188 |
| 10 | $PhCH_2CH_2$ | 233 |
| 11 | $PhCH=CHCH_2$ | 228 |

EXAMPLE 12

Preparation of 5-Phenylamido-6-Azaindole-2'-Carboxylic Acid

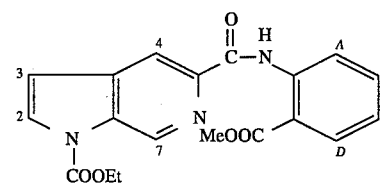

-continued

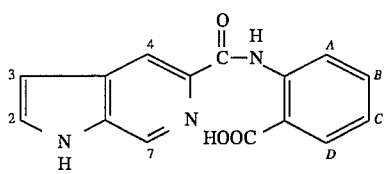

12

The acid ($R_1=R_3=R_4=H$, $R_2=OH$) (31.2 mg, 0.19 mmol) is dissolved in 3 ml of dry tetrahydrofuran to which 120 μl of distilled triethylamine are added. The reaction mixture is cooled to 0° C. and 50 μl (0.64 mmol) of distilled ethyl chloroformate are added dropwise. The solution is allowed to return to room temperature and then the temperature is brought to 40° C. The progress of the reaction is monitored by TLC (dichloromethane) and, when it is complete, the mixture is cooled and evaporated dryness. 5 ml of dry tetrahydrofuran and 26 μl (0.20 mmol) of methyl anthranilate are added thereto and the mixture is brought to reflux. The progress of the reaction is monitored by TLC (dichloromethane) and, when it is complete, the mixture is cooled and evaporated to dryness. The residue is taken up in dichloromethane and basified with a saturated sodium bicarbonate solution. The aqueous phase is extracted with dichloromethane. The organic phases are combined and washed with water, then a saturated sodium chloride solution and dried over magnesium sulfate. The solvent is evaporated under vacuum, leaving a residue which is chromatographed on a preparative plate (dichloromethane). Compound 16 is crystallized from a mixture of dichloromethane and n-Hexane (31.2 mg, 44%).

M.p. (dichloromethane/n-Hexane)=198°–199° C.

According to the same method, but with the corresponding aromatic amines, the following compounds were obtained:

| Examples | R | °M.p. |
|---|---|---|
| 13 | H | 225 |
| 14 | 3-COOH | 310 (decomp) |
| 15 | 4-COOH | 305 (decomp) |

Compound 16 (31 mg, 0.08 mmol) is dissolved in 5 ml of 10% aqueous ethanol to which 420 μl of 1N sodium hydroxide solution are added and the mixture is brought to reflux. After one hour, the reaction mixture is complete (95/5 dichloromethane/ethanol). The reaction mixture is cooled and the ethanol is evaporated. A few drops of water are added and the acid 12 is precipitated by controlled addition of acetic acid. After leaving overnight at 4° C., the precipitate is filtered, washed with water and dried to give 21.5 mg (91%) of acid 12.

M.p. ($H_2O$)=286°–297° C.

BIOLOGICAL PROPERTIES

A—In Vitro Tests on Cortex Membrane

The compounds of Examples 1 to 14 were tested on rat cortex membrane in order to determine their affinity for the benzodiazepine receptor.

The measurements are summarized in the table below.

| Examples | $IC_{50}$ (nM) |
|---|---|
| 1 | 750 |
| 2 | 1500 |
| 3 | 65 |
| 4 | 100 |
| 5 | 75 |
| 6 | 1200 |
| 7 | 1300 |
| 8 | 300 |
| 9 | 10000 |
| 10 | 8 |
| 11 | 150 |
| 12 | 300 |
| 13 | 7000 |
| 14 | 5500 |
| 15 | 2300 |

B—Pharmacological Property of the Compound of Example 1 Determination of the Pharmacological Profile This study consists of an electrophysiological test on Xenopus oocyte. The cells of chicken optical lobes fortuitously have a good response to GABA. The total RNAs are extracted therefrom and passed through an oligo(dT) affinity column, thus making it possible to separate the crude messenger RNAs therefrom, because the latter have a poly(A) end tail which will combine by complementarity with the oligo(dT) residues of the column. These messenger RNAs will then be injected into a Xenopus oocyte, which is only a one and only cell. These oocytes will then be incubated and, in two days, the messenger RNAs will be expressed and will thus, by virtue of the cell machinery of the oocyte, have produced GABA receptor/benzodiazepine receptor/chloride channel complexes. These large protein entities will then migrate in the cell and will reach the membrane, thus making it possible for this receptor and the transmembrane ion channel which is combined with it to take its place.

The oocyte is then placed in a $10^{-5}M$ GABA bath in Ringer solution and two microelectrodes A and B are introduced therein, a third microelectrode being placed outside the cell to act as reference. Microelectrode A will be used to measure the potential difference (PD) between the interior and the exterior of the oocyte. A PD of 60 mV is imposed on the oocyte and the microelectrode B will be used to maintain this desired PD.

By perfusing an agonist such as diazepam, the latter and the GABA present in the medium will exert an allosteric effect at the level of the receptor with, as corollary, opening of the ion channel. There will therefore be entry of chloride into the oocyte and the PD will greatly increase. On the other hand, an inverse agonist such as β-CCM will cause a reduction in the binding of the GABA to the receptor with, as consequence, a reduction in the time of opening of the chloride channel and a lower PD.

An antagonist will occupy the binding site of the benzodiazepine receptor but will have no effect on the binding of the GABA. The opening of the chloride channel will therefore not be disturbed and the PD will not vary.

Compound 1 was perfused in the medium bathing the oocyte at a concentration of $10^{-6}M$, causing, with respect to the great increase of the diazepam and the significant reduction of the β-CCM, a slight reduction of the PD. Molecule 1 is therefore a partial inverse agonist, whereas ZK 91296 is a partial agonist.

IN VIVO TESTS

Compound 1 was tested first for its convulsant properties. The test was carried out on 14 mice (5 males and 9 females) aged two months belonging to the ABP/Le strain. This particular strain is very sensitive to convulsions induced by β-carbolines. Compound 1 was administered intraperitoneally at a dose of 20 mg/kg and observation took place after 30 minutes. None of the mice showed the least convulsion. The compound is therefore not convulsant.

Compound 1 was then tested on learning. This test, passive avoidance with learning in a single test, was carried out on 30 female Swiss mice aged two months. Compound 1 was administered to 15 mice at a dose of 20 mg/kg, the other 15 receiving an injection of physiological serum.

The equipment consists of a white box connected to a black box by a door. The white box is lit by a 100 W lamp placed at a distance of 25 cm and the black box, into which the mouse will spontaneously go because she feels safe in the darkness, contains an electrified metal floor. The boxes are coated with the smell of mice by an animal placed inside before each of the two series of 15 mice.

The test takes place in two sessions: the first is the learning and the second, which takes place 24 hours afterwards, is the avoidance test proper.

Ten minutes before learning, the marked mice receive an intraperitoneal injection of physiological serum or of Compound 1. The injection is carried out with the test in order to verify if the molecule tested acts on the memory at the level of the acquisition phenomenon. If the phase of retention of the information had been studied, the injection would have taken place after the learning test. The mice were then placed one by one in the illuminated white box and the arrival time in the black box is recorded. This time is on average 24 seconds and the criterion used is that the four paws of the mouse are inside the black box. At this precise moment, an electrical shock of 75 µA of direct current is triggered for two seconds.

After 24 hours, the avoidance test takes place: the mouse is placed in the white box and whether or not the mouse enters the black box in three minutes is recorded without any electrical shock being caused. If the mouse enters the black box in less than three minutes, the molecule tested has not improved the acquisition of the information "black box= electric shock" but if the time recorded is greater than three minutes, the molecule is assumed to have acted.

|  | <3 mn | >3 mn |
|---|---|---|
| Treated | 4 | 11 |
| Untreated | 8 | 7 |

It is recorded that in the animals treated with the molecule, a majority (75%) of them learnt to avoid the electric shock. The memory-enhancing effect of the compound during the passive avoidance test with learning in a single test has therefore been revealed.

We claim:

1. A 6-azaindole compound of the formula:

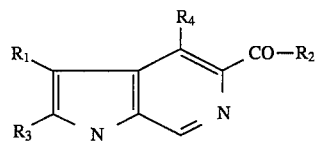

in which:

$R_1$ represents the hydrogen atom or a group $R_5$—O—$CH_2$— in which $R_5$ corresponds to an alkyl radical or to a group of formula Ar—Z, in which:

Z is a divalent alkyl or alkenyl radical having from 1 to 5 atoms,

Ar is an optionally substituted phenyl radical, $R_2$ is an alkoxy, cycloalkoxy, aryloxy, aralkoxy, N-alkyl-substituted amino, N-cycloalkyl-substituted amino or N-phenyl-substituted amino radical, wherein the aromatic rings are optionally substituted, $R_3$ and $R_4$ independently represent an hydrogen atom or an alkyl radical, with the exception of the compound where $R_1$, $R_3$ and $R_4$ are an hydrogen atom and $R_2$ is the N-(2-carboxyphenyl)amino radical, or its pharmacologically acceptable salt.

2. A 6-Azaindole compound according to claim 1, characterized in that Ar—Z corresponds to a group:

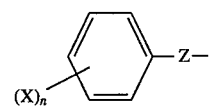

II in which:

X is a weakly hindered electron-donating radical, n is zero or a positive integer less than 6, wherein X can be identical or different when n is greater than 1.

3. A 6-Azaindole compound according to claim 2, characterized in that X is selected from halogen, nitro, cyano, optionally halogenated alkoxy, optionally halogenated $C_1$-$C_3$ alkyl, or linear propyl.

4. A 6-Azaindole compound according to claims 2 to 3, characterized in that n is 0, 1, 2 or 3.

5. A 6-Azaindole compound according to claim 1, characterized in that $R_1$ corresponds to the group of formula III:

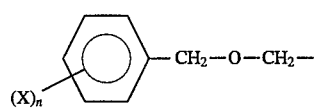

III in which:

X is a weakly hindered electron-donating radical, n is zero or a positive integer less than 6, wherein X can be identical or different when n is greater than 1, or $R_1$ is a methyl group substituted by an alkoxy radical.

6. A 6-Azaindole compound according to claim 5, characterized in that $R_2$ is $C_1$-$C_6$ alkoxy group.

7. A 6-Azaindole compound according to claim 1, characterized in that $R_1$ is a hydrogen atom.

8. A 6-Azaindole compound according to claim 7, characterized in that $R_2$ is N-alkyl-substituted amino, N-cycloalkyl-substituted amino or N-phenyl-substituted amino.

9. A 6-Azaindole compound according to claim 8, characterized in that $R_2$ is N-phenylamino optionally substituted by one or more radicals selected from the group consisting of carboxy, sulfonate and acid phosphonate radicals.

10. A medicament consisting of a compound according to claim 1 wherein $R_1$, $R_3$ and $R_4$ are hydrogen and $R_2$ is N-(2-carboxyphenyl)amino.

11. A pharmaceutical composition containing at least one medicament according to claim 10 and an acceptable vehicle.

12. A 6-Azaindole compound according to claim 1, characterized in that Z is selected from $-CH_2$, $-CH_2-CH_2-$, $-CH=CH-$ or $-CH=CH-CH_2$.

13. A 6-Azaindole compound according to claim 3, characterized in that X is selected from $CF_3$ or $SO_3H$.

14. A 6-Azaindole compound according to claim 9, characterized in that $R_2$ is N-phenylamino which is optionally substituted by one or more radicals chosen from carboxy, sulfonate or acid phosphonate radicals.

* * * * *